United States Patent [19]

Honda et al.

[11] Patent Number: 5,380,359
[45] Date of Patent: Jan. 10, 1995

[54] COSMETICS BASED ON NATURALLY DERIVED MELANIN-COATED PIGMENTS

[75] Inventors: Shinkichi Honda, Abiko; Yoichiro Takekoshi, Tsuchiura; Yoichiro Arai, Niihari, all of Japan

[73] Assignee: Kyowa Hakko Kogyo Co., Ltd., Tokyo, Japan

[21] Appl. No.: 150,114

[22] Filed: Nov. 24, 1993

[30] Foreign Application Priority Data

Mar. 31, 1992 [JP] Japan ................... 4-077848
Oct. 15, 1992 [WO] WIPO ................. PCT/JP92/01338

[51] Int. Cl.$^6$ .................................................. C09C 1/32
[52] U.S. Cl. ................................. 106/414; 106/416; 106/417; 106/437; 106/447; 106/448; 106/460; 106/467; 106/468; 106/469; 106/470; 106/471; 106/482; 106/487; 106/491; 106/493; 106/499; 106/506; 424/69
[58] Field of Search ............... 106/499, 506, 400, 401, 106/414, 415, 416, 417, 437, 447, 448, 460, 465, 467, 468, 469, 470, 471, 482, 487, 491, 493; 424/69

[56] References Cited

U.S. PATENT DOCUMENTS

| | | | |
|---|---|---|---|
| 4,961,754 | 10/1990 | Grollier | 8/423 |
| 5,242,689 | 9/1993 | Yoshihara et al. | 106/499 |
| 5,288,494 | 2/1994 | Yoshihara et al. | 106/502 |

FOREIGN PATENT DOCUMENTS

| | | |
|---|---|---|
| 0379409 | 7/1990 | European Pat. Off. |
| 54289 | 12/1981 | Japan |
| 1-092273 | 4/1989 | Japan |
| 1-032263 | 6/1989 | Japan |
| 2-232264 | 9/1990 | Japan |
| WO16189 | 10/1992 | WIPO |

OTHER PUBLICATIONS

G. M. Gadd, FEMS Microb. Lett., vol. 9 (1980) 237:40, no month.
B. I. Rowley et al., Trans. Br. mycol. Soc., vol. 70, No. 3 (1978) 453:55 no month.
G. Hintermann et al., Mol. Gen. Genet., vol. 200 (1985) 422:32, no month.

Primary Examiner—Karl Group
Assistant Examiner—Scott L. Hertzog
Attorney, Agent, or Firm—Fitzpatrick, Cella, Harper & Scinto

[57] ABSTRACT

A melanin-coated pigment obtained by coating a carrier with a readily alkali-soluble natural melanin, and a cosmetic containing the pigment are provided. The melanin-coated pigment is highly safe and has high coloring and high saturation tone, and a cosmetic which contains it is also expected to have ultraviolet-ray-absorbing and anti-oxidizing effects.

6 Claims, 3 Drawing Sheets

COSMETICS BASED ON NATURALLY DERIVED MELANIN-COATED PIGMENTS

TECHNICAL FIELD

The present invention relates to a melanin-coated pigment obtained by coating a carrier with a readily alkali-soluble natural melanin, and a cosmetic containing the pigment.

BACKGROUND ART

Melanin is a dark brown or black pigment which is known to have ultraviolet-ray-absorbing and other properties.

Sepia melanin, extracted from the ink bags of cuttlefish, is known as a black pigment which is dispersed in a system and used in cosmetics in the same manner as carbon black and black iron oxide (Japanese Published Unexamined Patent Application No. 53211/80).

U.S. Pat. No. 4,961,754 discloses a powder prepared by modifying the surface of an inorganic powder with a synthetic melanin produced by an oxidative polymerization reaction of a compound having an indole skeleton, and cosmetics containing the powder.

Powders prepared by modifying the powder surface with a polymerized synthetic melanin are not suitable for use in cosmetics in respect of safety because of skin irritation due to residual low molecular weight compounds, free monomers and oxidizing catalysts such as potassium iodide and hydrogen peroxide from the synthesis process.

Further, sepia melanin is insoluble in acids or alkalis and is poorly soluble in solvents, which makes its separation and purification difficult, and thus it is not suitable for use in cosmetics, either.

It has been discovered that melanin adsorbed on a carrier can be used for adding color, particularly to cosmetics, as a flesh- or gray-colored pigment which differs from the color of melanin.

DISCLOSURE OF THE INVENTION

The present invention provides a melanin-coated pigment obtained by coating a carrier with a readily alkali-soluble natural melanin, and cosmetics containing the pigment.

As the carrier, any powder which is insoluble in water, oil, and the like and can adsorb melanin may be used. Preferred examples are inorganic and organic pigments.

The inorganic pigment consists of an inorganic compound. Examples of the inorganic pigment include titanium dioxide, talc, sericite, mica, micaceous titanium, montmorillonite, kaolin, alumina, magnesium oxide, cesium oxide, silica, muscovite, barium sulfate, aluminum silicate, aluminum magnesium silicate, sodium magnesium silicate, calcium silicate, iron oxide, calcium carbonate, pumice powder, and ultramarine.

The organic pigment consists of an organic compound. A number of dyes and pigments may be used as the organic pigment. In addition, as the inorganic or organic powder may be used resins such as nylon 6, nylon 6.6, nylon powder, and silicon resin, as well as cellulose, crystalline cellulose, silk powder, and the like.

These carriers have a particle diameter of 0.01-100 microns and may be used alone or in combination.

The readily alkali-soluble natural melanin according to the present invention refers to alkali-soluble melanins derived from microorganisms and plants. Preferred examples include melanins produced by microorganisms belonging to the genus Aureobasidium, Aspergillus, and Streptomyces (hereinafter referred to as "microbial melanin"), which can be obtained by known methods, for example, the methods described in FEMS Microbiology Letters, 9, 237–240, 1980; Trans. Br. Mycol. Soc., 70 (3), 453–455, 1978; and Mol. Gen. Genet., 200, 422–432, 1985.

The readily alkali-soluble natural melanin to be used in the present invention not only dissolves in aqueous solutions of alkalis such as aqueous ammonia and aqueous solutions of sodium hydroxide, potassium hydroxide and calcium hydroxide, but is also soluble in organic solvents such as triethylamine, triethanolamine, ammonia-containing methanol, ethanol, isopropyl alcohol, propylene glycol, 1,3-butylene glycol, and glycerin, and may be subjected to nonaqueous treatment.

The melanin-coated pigment according to the present invention can be prepared by applying a known method of adsorbing a component of a solution on a carrier. For example, it can be obtained by the following method.

The above-mentioned melanin is dissolved in an alkali solution such as 0.01–6.0N sodium hydroxide, potassium hydroxide or ethanolamine. A carrier is added thereto and the mixture is stirred. To the resulting colored suspension is gradually added an acidic solution such as 0.01–6.0N hydrochloric acid with stirring, until the melanin is sufficiently adsorbed on the carrier. By lowering the pH to 1–4 the supernatant becomes clear. The solution is subjected 2–5 times to filtration and washing with a 5- to 10-fold amount of water. Then, the residue is dried and the dried product is crushed to obtain a powdery melanin-coated pigment 0.05–50 μm in size.

The carrier is coated with 0.01–50 w/w % of the readily alkali-soluble natural melanin.

The thus obtained melanin-coated pigment can be used as a flesh- or gray-colored pigment in paint, ink, cosmetics, and the like. When used in cosmetics, it is expected to be also effective in absorbing ultraviolet rays.

A melanin-coated pigment having the desired tint may be obtained by experimentally adjusting the type of carrier and the amount of the melanin coating. Such experiments may be easily carried out by a person skilled in the art.

The malanin-coated pigment of the present invention may be employed in cosmetics in any desired form, for example, solutions, emulsions, powders, jellies, and solid preparations. Examples of such cosmetics include skin-care products such as lotions, emulsions, creams, soap and pack; make-up products such as lipsticks, foundations, eye-shadows, and eye-liners; and hair-care products such as shampoos and rinses.

Cosmetics according to the present invention may comprise various components which are generally used in cosmetics, for example, fats and oils, hydrocarbons, waxes, fatty acids, synthetic esters, alcohols, surfactants, thickeners, moisturizers, preservatives, fragrances, pigments, ultraviolet absorbers, chemicals, and water, which are selected depending upon the form of cosmetics.

Examples of the fats and oils are jojoba oil, castor oil, olive oil, soybean oil, coconut oil, palm oil, cacao butter, mink oil, turtle oil, fatty acid diethanolamide, and shea butter.

Examples of the hydrocarbons are liquid paraffin, solid paraffin, vaseline, microcrystalline wax, and squalane.

Examples of the waxes are beeswax, Japan wax, lanolin, carnauba wax, candelilla wax, and hydrocarbon wax.

Examples of the fatty acids are myristic acid, palmitic acid, stearic acid, oleic acid, and isostearic acid.

Examples of the synthetic esters are isopropyl myristate, isopropyl palmitate, butyl oleate, myristyl myristate, octyldecyl myristate, propylene glycol monostearate, myristyl lactate, isostearyl malate, glycerin monostearate, distearyldimethyl ammonium chloride, and acetyltributyl citrate.

The fats and oils, hydrocarbons, waxes, fatty acids and synthetic esters are usually contained in the cosmetics in a total amount of 0.01–70 w/w %.

Examples of the alcohols are ethanol, 1,3-butylene glycol, propylene glycol, lauryl alcohol, cetanol, stearyl alcohol, oleyl alcohol, and denatured alcohol. The alcohols are contained in the cosmetics in an amount of 0.01–60 w/w %.

Examples of the surfactants are polyoxyethylene (60) hardened castor oil, sodium lauryl sulfate, polyoxyethylene glyceryl pyroglutamate isostearate, sodium alkylbenzene sulfonate, polyoxyethylene (10) stearyl ether, dialkyl sulfosuccinate, cetyl pyridinium bromide, n-octadecyl trimethylammonium chloride, monoalkyl phosphate, N-acylglutamic acid, sucrose fatty acid ester, glyceryl isostearate, polyoxyethylene (20) sorbitan monostearate, sorbitan sesquioleic acid ester, polyoxyethylene (20) sorbitan monooleate, sorbitan sesquioleate, glycerin monostearate, polyoxyethylene cetyl ether phosphate, polyoxyethylene lauryl ether sodium sulfate, polyoxyethylene-reduced lanolin, polyoxyethylene (20) sorbitan tristearate, polyoxyethylene (20) sorbitan trioleate, and soybean phospholipid. The surfactants are contained in the cosmetics in an amount of 0.01–40 w/w %.

Examples of the thickeners are carboxyvinyl polymer, methylpolysiloxane, dextran, carboxymethyl cellulose, carrageenin, hydroxymethyl cellulose, vinyl acetate resin emulsion, and polyacrylic acid ester emulsion. The thickeners are contained in the cosmetics in an amount of 0.01–5 w/w %.

Examples of the moisturizers are glycerin, propylene glycol, 1,3-butylene glycol, pyrrolidonecarboxylic acid, lactic acid, hyaluronic acid, collagen, N-acetyl-L-glutamine, triethanolamine, citric acid, and sodium citrate. The moisturizers are contained in the cosmetics in an amount of 0.01–30 w/w %.

Examples of the preservatives are benzoic acid, salicylic acid, dehydroacetic acid or salts thereof, phenols such as p-hydroxybenzoate, 2,4,4'-trichloro-2'-hydroxydiphenyl ether, and 3-trifluoromethyl-4,4'-dichlorocarbanilide. The preservatives are contained in the cosmetics in an amount of 0.01–0.5 w/w %.

Any fragrances which are conventionally used in cosmetics may be used.

Examples of the pigments to be added to the cosmetics are titanium dioxide, talc, sericite, mica, micaceous titanium, montmorillonite, kaolin, alumina, magnesium oxide, cesium oxide, silica, muscovite, barium sulfate, aluminum silicate, aluminum magnesium silicate, sodium magnesium silicate, calcium silicate, iron oxide, calcium carbonate, pumice powder, ultramarine, nylon 6, nylon 6.6, nylon powder, cellulose, crystalline cellulose, and silk powder. The pigments are contained in the cosmetics in an amount of 0.01–90 w/w %.

Examples of the ultraviolet absorbers are ethyl diisopropyl cinnamate, methyl diisopropyl cinnamate, glyceryl mono(2-ethylhexylate) di(p-methoxy) cinnamate, p-aminobenzoic acid, ethyl p-aminobenzoate, 4-tert-butyl-4'-methoxy-dibenzoylmethane, and 2-ethylhexyl p-dimethylaminobenzoate. The ultraviolet absorbers are contained in the cosmetics in an amount of 0.01–10 w/w %.

Examples of the chemicals are vitamin E, vitamin C or a derivative thereof, licorice extract, dipotassium glycyrrhizinate, and placenta liquid. The chemicals are contained in the cosmetics in an amount of 0.01–5 w/w %.

The melanin-coated pigment according to the present invention may be used alone, or a mixture of two or more pigments may be used. The pigment is contained in the cosmetics in an amount of 0.01–90% by weight.

The cosmetics containing the melanin-coated pigment according to the present invention can be prepared in the same manner as in known methods for the production of cosmetics, except that a portion or all of the pigments used is replaced by the pigment of the present invention.

The microbial melanin to be used in the present invention is highly safe and has a wide band of absorption in the ultraviolet region. The pigment coated with the microbial melanin has high coloring and saturation tones, and the cosmetics which contain the pigment have an excellent ultraviolet-ray-blocking effect.

BEST MODE FOR CARRYING OUT THE INVENTION

Examples, test examples and comparative examples are provided below. The percentages indicated in the Examples are % by weight.

EXAMPLE 1

Preparation of Melanin-Coated Pigment

*Streptomyces aureofaciens* (ATCC 10762) cells were inoculated into 300 ml of a seed medium (2.0% starch, 0.5% peptone, 0.9% corn steep liquor, 0.1% CaCO$_3$, pH 5.5) in a 2-liter Erlenmeyer flask, and subjected to shaking culture (rotation: 200 rpm) at 30° C. for 3 days.

The resulting seed culture was inoculated into 30 liters of a production medium (5.0% starch, 6.0% soybean powder, 0.75% lysine hydrochloride, 50 mg/l $Mg_2SO_4.7H_2O$, 50 mg/l $CuSO_4.5H_2O$, 50 mg/l $ZnSO_4.7H_2O$, 0.1% $CaCO_3$, 4.0% soybean oil) in a 30-liter jar fermenter, and stirring culturing with aeration (rotation: 425 rpm, aeration: 10 l/min) was carried out at 27° C. for 10 days.

To 10 liters of the resulting culture was added 40 g of sodium hydroxide, the mixture was subjected to centrifugation (8,000 rpm, 30 minutes), and the supernatant was separated. To the obtained cells was added 1 liter of 0.1N aqueous sodium hydroxide, followed by centrifugation (8,000 rpm, 30 minutes) to obtain a supernatant. This supernatant was combined with the previously separated supernatant, and 150 ml of 10N hydrochloric acid was added thereto, followed by centrifugation (8,000 rpm, 30 minutes). To the obtained residue was added 1 liter of 1N sodium hydroxide, and the mixture was stirred and then filtered to obtain a filtrate. To the filtrate was added 100 ml of 10N hydrochloric acid, and the mixture was subjected to centrifugation (8,000 rpm, 30 minutes). The obtained residue was subjected three times to a washing procedure consisting of addition of 1 liter of purified water and centrifugation (8,000 rpm, 30 minutes) to obtain 60 g of crude microbial melanin.

To 1.4 g of the obtained crude microbial melanin was added 50 ml of 6N hydrochloric acid, and the mixture was heated at 110° C. for 48 hours for hydrolysis. The reaction mixture was dissolved in 100 ml of 6N sodium hydroxide, and the solution was filtered through a glass fiber filter paper. To the filtrate was added 200 ml of 6N hydrochloric acid, and a precipitate was separated by sedimentation. After 1 liter of water was added to the sediment, a precipitate was again separated by sedimentation and was freeze-dried to obtain 1 g of purified melanin. The purified melanin (1 g) was dissolved uniformly in 3,000 g of 0.1N aqueous sodium hydroxide. Then, 100 g of a carrier (titanium dioxide, mica, talc, nylon powder or sericite) was added thereto and uniformly dispersed, and 400 g of 1N hydrochloric acid was slowly added thereto with stirring. The mixture was filtered, washed with water, and dried, and the dried product was crushed to obtain a melanin-coated pigment 5 μm in size.

EXAMPLE 2

Preparation of Melanin-Coated Pigment

The purified melanin (0.1 g) obtained in Example 1 was dissolved uniformly in 100 ml of 0.1N aqueous potassium hydroxide. Then, 5 g of titanium dioxide was added to the solution and dispersed uniformly therein, and 12 g of 1 N sulfuric acid was slowly added thereto with stirring to adjust the pH to 7. Fifty milliliters of purified water containing 0.5 g of barium chloride was added to the mixture with stirring, and then 3 g of 1N sulfuric acid was slowly added thereto. The resulting mixture was filtered, washed with water and dried, and the dried product was crushed to obtain a melanin-coated pigment 5 μm in size.

EXAMPLE 3

Non-Aqueous Preparation of Melanin-Coated Pigment

The purified melanin (0.1 g) obtained in Example 1 was dissolved uniformly in 100 ml of methanol containing 0.5 g of triethylamine. Then, 5 g of titanium dioxide was added to the solution and dispersed uniformly therein. The solvent was distilled off, and the dried product was crushed to obtain a melanin-coated pigment 5 μm in size.

EXAMPLE 4

Non-Aqueous Preparation of Melanin-Coated Pigment (Hydrophobic Treatment with a Silicon Derivative)

To a uniform dispersion of 0.1 g of the purified melanin obtained in Example 1, 0.5 g of triethylamine, 100 ml of methanol and 5 g of titanium dioxide was added 20 ml of isopropyl alcohol containing 0.5 g of methylhydrogen polysiloxane to obtain a uniform solution. The solvent was distilled off, and the dried product was heated at 160° C. for one hour and then crushed to obtain a hydrophobic melanin-coated pigment 5 μm in size.

EXAMPLE 5

Preparation of a Solid-Type Foundation

A solid-type foundation having the following composition was prepared using the melanin-coated pigments obtained in Example 1.

| | |
|---|---|
| (2) Melanin-coated mica | 55.0% |
| (3) Melanin-coated talc | 22.0% |
| (4) Iron oxide | 1.0% |
| (5) Liquid paraffin | 6.0% |
| (6) Lanolin | 4.0% |
| (7) Sorbitan sesquioleic ester | 1.5% |
| (8) Fragrance | 0.7% |
| (9) p-Hydroxybenzoate | 0.8% |

A uniform solution of the ingredients (6)–(9) in the ingredient (5) was added to the ingredients (1)–(4) while they were being mixed in a blender. The resulting mixture was crushed, and the obtained powder was subjected to compression molding to prepare a solid-type foundation.

EXAMPLE 6

Preparation of a Liquid Foundation

A liquid foundation having the following composition was prepared using the melanin-coated pigments obtained in Example 1.

| | |
|---|---|
| (1) Melanin-coated titanium dioxide | 3.0% |
| (2) Melanin-coated mica | 2.0% |
| (3) Melanin-coated nylon powder | 0.5% |
| (4) Iron oxide | 1.0% |
| (5) Liquid paraffin | 3.0% |
| (6) Beeswax | 2.0% |
| (7) Carnauba wax | 0.2% |
| (8) Squalane | 3.0% |
| (9) Polyoxyethylene (20) sorbitan monooleate | 0.5% |
| (10) Sorbitan sesquioleate | 1.0% |
| (11) Glycerin monostearate | 3.0% |
| (12) Polyoxyethylene cetyl ether phosphate | 0.2% |
| (13) 1,3-Butylene glycol | 12.0% |
| (14) Carboxyvinyl polymer (1% aqueous solution) | 10.0% |
| (15) Triethanolamine | 0.1% |
| (16) Fragrance | 0.3% |
| (17) p-Hydroxybenzoate | 0.2% |
| (18) Purified water | 58.0% |

The ingredients (1)–(4), (12) and (13) were mixed and uniformly dispersed using a 3-roll mill (pigment portion). The ingredients (5)–(11), (16) and (17) were heated for dissolution at 80° C. and the ingredients (14), (15) and (18) which had been uniformly mixed by heating at 80° C. and the pigment portion were added thereto. The resulting mixture was emulsified with a homomixer, and then cooled to obtain a liquid foundation.

EXAMPLE 7

Preparation of a Lipstick

A lipstick having the following composition was prepared using the melanin-coated pigments obtained in Example 1.

| | | |
|---|---|---|
| (1) | Hydrocarbon wax | 5.0% |
| (2) | Candelilla wax | 2.0% |
| (3) | Glyceryl isostearate | 35.0% |
| (4) | Liquid paraffin | 45.0% |
| (5) | Melanin-coated titanium dioxide | 3.0% |
| (6) | Melanin-coated mica | 6.7% |
| (7) | Organic pigment (Pigment Red 3 aluminum lake) | 3.0% |
| (8) | Fragrance | 0.3% |

The ingredients (4)–(7) were mixed and kneaded with a 3-roll mill to obtain a uniform mixture, and the ingredients (1)–(3) and (8) were added thereto, followed by heating for dissolution until the temperature reached 85° C. The mixture was stirred to obtain a uniform mixture, which was then charged into a container to prepare a lipstick.

EXAMPLE 8

Preparation of an Eye-Liner

An eye-liner having the following composition was prepared using the melanin-coated pigments obtained in Example 1.

| | | |
|---|---|---|
| (1) | Ultramarine | 2.0% |
| (2) | Melanin-coated talc | 4.0% |
| (3) | Melanin-coated mica | 4.0% |
| (4) | Vinyl acetate resin emulsion | 45.0% |
| (5) | Glycerin | 5.0% |
| (6) | Polyoxyethylene (20) sorbitan monooleate | 1.0% |
| (7) | Carboxymethyl cellulose (10% aqueous solution) | 15.0% |
| (8) | Acetyltributyl citrate | 1.0% |
| (9) | Purified water | 22.7% |
| (10) | Fragrance | 0.2% |
| (11) | Dehydroacetic acid | 0.1% |

The ingredients (5), (6) and (9) were heated for dissolution, and the ingredients (1)–(3) were added thereto, followed by mixing using a colloid mill to obtain a uniform mixture. The ingredients (4), (6)–(8), (10) and (11) were added thereto and the mixture was uniformly dispersed with a homomixer to obtain an eye-liner.

EXAMPLE 9

Preparation of an Eyebrow Pencil

An eyebrow pencil having the following composition was prepared using the melanin-coated pigments obtained in Example 1.

| | | |
|---|---|---|
| (1) | Melanin-coated titanium dioxide | 3.0% |
| (2) | Melanin-coated talc | 22.0% |
| (3) | Melanin-coated sericite | 22.4% |
| (4) | Melanin-coated mica | 15.0% |
| (5) | Ultramarine | 2.0% |
| (6) | Japan wax | 25.0% |
| (7) | Vaseline | 7.0% |
| (8) | Squalane | 3.0% |
| (9) | p-Hydroxybenzoate | 0.3% |

*-continued*

| | | |
|---|---|---|
| (10) | Vitamin E | 0.3% |

The ingredients (1)–(5) were uniformly mixed using a blender (pigment portion). The ingredients (6)–(10) were heated for dissolution and stirred to obtain a uniform mixture. The pigment portion was added thereto, and the mixture was kneaded and formed into a stick to obtain an eyebrow pencil.

EXAMPLE 10

Preparation of a Mascara

A mascara having the following composition was prepared using the melanin-coated pigment obtained in Example 1.

| | | |
|---|---|---|
| (1) | Melanin-coated mica | 10.0% |
| (2) | Polyacrylic acid ester emulsion | 27.0% |
| (3) | Solid paraffin | 7.0% |
| (4) | Lanolin | 7.0% |
| (5) | Sorbitan sesquioleate | 3.0% |
| (6) | p-Hydroxybenzoate | 0.3% |
| (7) | Fragrance | 0.2% |
| (8) | Purified water | 45.5% |

The ingredient (8) was dispersed in the ingredient (1) with a homomixer, and the dispersion was uniformly mixed with the ingredient (2). The mixture was added to a mixture of the ingredients (3)–(7) which had been heated at 70° C. for dissolution, and the resulting mixture was emulsified and dispersed with a homomixer to obtain a mascara.

EXAMPLE 11

Preparation of Sunscreen Emulsion

A sunscreen emulsion having the following composition was prepared using the melanin-coated pigment obtained in Example 1.

| | | |
|---|---|---|
| (1) | Melanin-coated talc | 0.5% |
| (2) | Soybean phospholipid | 0.1% |
| (3) | 1,3-Butylene glycol | 5.0% |
| (4) | 2-Ethylhexyl p-dimethylaminobenzoate | 0.1% |
| (5) | Liquid paraffin | 2.0% |
| (6) | Glycerin monostearate | 1.0% |
| (7) | Carboxyvinyl polymer (1% aqueous solution) | 10.0% |
| (8) | Triethanolamine | 0.1% |
| (9) | p-Hydroxybenzoate | 0.2% |
| (10) | Fragrance | 0.2% |
| (11) | Purified water | 80.8% |

The ingredients (1)–(3) were mixed and uniformly dispersed with a 3-roll mill (pigment portion). The ingredients (4)–(6) were heated at 80° C. for dissolution (oil phase). The ingredients (7)–(11) were heated at 80° C. for dissolution, the pigment portion was added thereto, and the resulting mixture was stirred to obtain a uniform mixture (water phase). The water phase was added to the oil phase, and the mixture was emulsified with a homomixer and then cooled to obtain a sunscreen emulsion.

EXAMPLE 12

Preparation of a Sunscreen Cream

A sunscreen cream having the following composition was prepared using the melanin-coated pigment obtained in Example 1.

| | | |
|---|---|---|
| (1) | Melanin-coated sericite | 1.0% |
| (2) | Beeswax | 2.0% |
| (3) | Carnauba wax | 0.2% |
| (4) | Cetanol | 3.0% |
| (5) | Liquid paraffin | 3.0% |
| (6) | 1,3-Butylene glycol | 5.0% |
| (7) | POE (20) sorbitan tristearate | 1.5% |
| (8) | Glycerin monostearate | 3.0% |
| (9) | Carboxyvinyl polymer (1% aqueous solution) | 10.0% |
| (10) | Triethanolamine | 0.1% |
| (11) | p-Hydroxybenzoate | 0.2% |
| (12) | Fragrance | 0.3% |
| (13) | Purified water | 70.7% |

The ingredients (2)–(7) were heated at 80° C. for dissolution (oil phase). The ingredients (1) and (8)–(13) were heated at 80° C. for dissolution and stirred to obtain a uniform mixture (water phase). The water phase was added to the oil phase, and the mixture was emulsified with a homomixer and then cooled to obtain a sunscreen cream.

EXAMPLE 13

Preparation of a Sunscreen Lotion

A sunscreen lotion having the following composition was prepared using the melanin-coated pigment obtained in Example 1.

| | | |
|---|---|---|
| (1) | Melanin-coated nylon powder | 0.5% |
| (2) | Glycerin | 1.0% |
| (3) | 1,3-Butylene glycol | 5.0% |
| (4) | Citric acid | 0.1% |
| (5) | Sodium citrate | 0.08% |
| (6) | POE (60) hardened castor oil | 1.0% |
| (7) | p-Hydroxybenzoate | 0.2% |
| (8) | Fragrance | 0.2% |
| (9) | Ethanol | 5.0% |
| (10) | Purified water | 86.92% |

The ingredients (1)–(5) and (10) were heated at 80° C. for dissolution and stirred to obtain a uniform mixture (water phase). The ingredients (6)–(9) were heated at 80° C. for dissolution (oil phase). The water phase was added to the oil phase with stirring, and the resulting uniform mixture was cooled to obtain a sunscreen lotion.

EXAMPLE 14

Preparation of a Sunscreen Cream

A sunscreen cream having the following composition was prepared using the melanin-coated pigments obtained in Example 1.

| | | |
|---|---|---|
| (1) | Melanin-coated titanium dioxide | 2.4% |
| (2) | Melanin-coated talc | 1.2% |
| (3) | Stearic acid | 1.0% |
| (4) | Cetanol | 0.5% |
| (5) | Shea butter | 0.05% |
| (6) | Castor oil | 0.7% |
| (7) | Methylpolysiloxane | 1.0% |
| (8) | Liquid paraffin | 1.0% |
| (9) | Natural vitamin E | 0.05% |
| (10) | Glycerin monostearate | 1.0% |
| (11) | POE (20) sorbitan trioleate | 0.2% |
| (12) | Soybean phospholipid | 0.2% |
| (13) | 2-Ethylhexyl p-dimethylaminobenzoate | 3.0% |
| (14) | 4-tert-Butyl-4'-methoxydibenzoylmethane | 2.0% |
| (15) | Triethanolamine | 0.7% |
| (16) | p-Hydroxybenzoate | 0.2% |
| (17) | 1,3-Butylene glycol | 4.2% |
| (18) | Carboxyvinyl polymer | 0.2% |
| (19) | Ethanol | 7.0% |
| (20) | Collagen | 0.05% |
| (21) | N-Acetyl-L-glutamine | 0.01% |
| (22) | Plant (hamamelis) extract | 0.7% |
| (23) | Purified water | 72.64% |

The ingredients (1), (2), (6), (11), (12) and (17) were mixed and uniformly dispersed with a 3-roll mill (pigment portion). The ingredients (3)–(5), (7)–(10), (13) and (14) were heated at 80° C. for dissolution (oil phase). The ingredients (15)–(18), (21) and (23) were heated at 80° C. for dissolution, the pigment portion was added thereto, and the resulting mixture was stirred to obtain a uniform mixture (water phase). The water phase was added to the oil phase, and the mixture was emulsified with a homomixer and then cooled, followed by mixing with the ingredients (19), (20) and (22) to obtain a sunscreen cream.

EXAMPLE 15

Preparation of a Sunscreen Cream

A sunscreen cream having the following composition was prepared using the melanin-coated pigment obtained in Example 2.

| | | |
|---|---|---|
| (1) | Melanin-coated barium sulfate | 1.0% |
| (2) | Beeswax | 2.2% |
| (3) | Cetanol | 3.0% |
| (4) | Liquid paraffin | 3.0% |
| (5) | 1,3-Butylene glycol | 5.0% |
| (6) | POE (20) sorbitan tristearate | 1.5% |
| (7) | Glycerin monostearate | 3.0% |
| (8) | Carboxyvinyl polymer (1% aqueous solution) | 10.0% |
| (9) | Triethanolamine | 0.2% |
| (10) | p-Hydroxybenzoate | 0.2% |
| (11) | Fragrance | 0.3% |
| (12) | Purified water | 70.6% |

The ingredients (2)–(6) were heated at 80° C. for dissolution (oil phase). The ingredients (1) and (7)–(12) were heated at 80° C. for dissolution and stirred to obtain a uniform mixture (water phase). The water phase was added to the oil phase, and the mixture was emulsified with a homomixer, and then cooled to obtain a sunscreen cream.

EXAMPLE 16

Preparation of a Sunscreen Emulsion

A sunscreen emulsion having the following composition was prepared using the melanin-coated pigment obtained in Example 3.

| | | |
|---|---|---|
| (1) | Melanin-coated titanium dioxide | 2.0% |
| (2) | Soybean phospholipid | 0.2% |
| (3) | 1,3-Butylene glycol | 3.0% |
| (4) | 2-Ethylhexyl p-dimethylaminobenzoate | 1.0% |
| (5) | Liquid paraffin | 2.0% |
| (6) | Glycerin monostearate | 1.0% |
| (7) | Carboxyvinyl polymer | 20.0% |

-continued

| | |
|---|---|
| (1% aqueous solution) | |
| (8) Triethanolamine | 0.5% |
| (9) p-Hydroxybenzoate | 0.2% |
| (10) Fragrance | 0.1% |
| (11) Purified water | 70.0% |

The ingredients (1)–(3) were mixed and uniformly dispersed-with a 3-roll mill (pigment portion). The ingredients (4)–(6) were heated at 80° C. for dissolution (oil phase). The ingredients (7)–(11) were heated at 80° C. for dissolution, the pigment portion was added thereto, and the resulting mixture was stirred to obtain a uniform mixture (water phase). The water phase was added to the oil phase, and the mixture was emulsified with a homomixer, and then cooled to obtain a sunscreen emulsion.

EXAMPLE 17

Preparation of a Lipstick

A lipstick having the following composition was prepared using the hydrophobic melanin-coated pigment obtained in Example 4.

| | |
|---|---|
| (1) Candelilla wax | 10.0% |
| (2) Solid paraffin | 15.0% |
| (3) Purified lanolin | 10.0% |
| (4) Liquid paraffin | 33.0% |
| (5) Castor oil | 20.0% |
| (6) Hydrophobic melanin-coated titanium dioxide | 3.0% |
| (7) Organic pigment (Pigment Red 3 aluminum lake) | 8.7% |
| (8) Fragrance | 0.3% |

The ingredients (5)–(7) were mixed and kneaded with a 3-roll mill to obtain a uniform mixture, and the ingredients (1)–(4) and (8) were added thereto, followed by heating for dissolution until the temperature reached 85° C. The mixture was stirred to obtain a uniform mixture, which was then charged into a container and cooled to obtain a lipstick.

TEST EXAMPLE 1

The ultraviolet-ray-absorbing effect of the microbial melanin upon ultraviolet irradiation is indicated below.

1) Survival curve of L929 fibroblasts upon ultraviolet (UVB) irradiation

Mouse-derived L929 fibroblasts were inoculated into wells of a 6-well microplate (product of Iwaki Glass Co.) to $2 \times 10^4$ cells/well, with 2 ml of MEM medium (product of Nissui Seiyaku Co.) containing 10% fetal calf serum, and were cultured in a 5% $CO_2$ incubator at 37° C. for 3 days. After the culturing, the MEM medium was removed, and the cells were washed with PBS (−) [composition: 8,000 mg of sodium chloride, 200 mg of potassium chloride, 1,150 mg of anhydrous sodium monohydrogenphosphate, 200 mg of anhydrous potassium dihydrogenphosphate, and 1 l of purified water (pH 7.5); the same shall apply hereinafter] (product of Takara Shuzo Co., Ltd.). Then, 1 ml of PBS (−) was poured into each well, followed by irradiation with UVB (wavelength: 300 nm; the same shall apply hereinafter) with varied intensity.

The UV lamp used was FL20S.E (maximum wavelength: 300 nm, product of TOSHIBA Co.), and the UVB intensity was measured using an ultraviolet intensity meter UVR-1 (Light receiver unit UVR-25, Tokyo Kogaku Kikai Co.).

Figure 1:
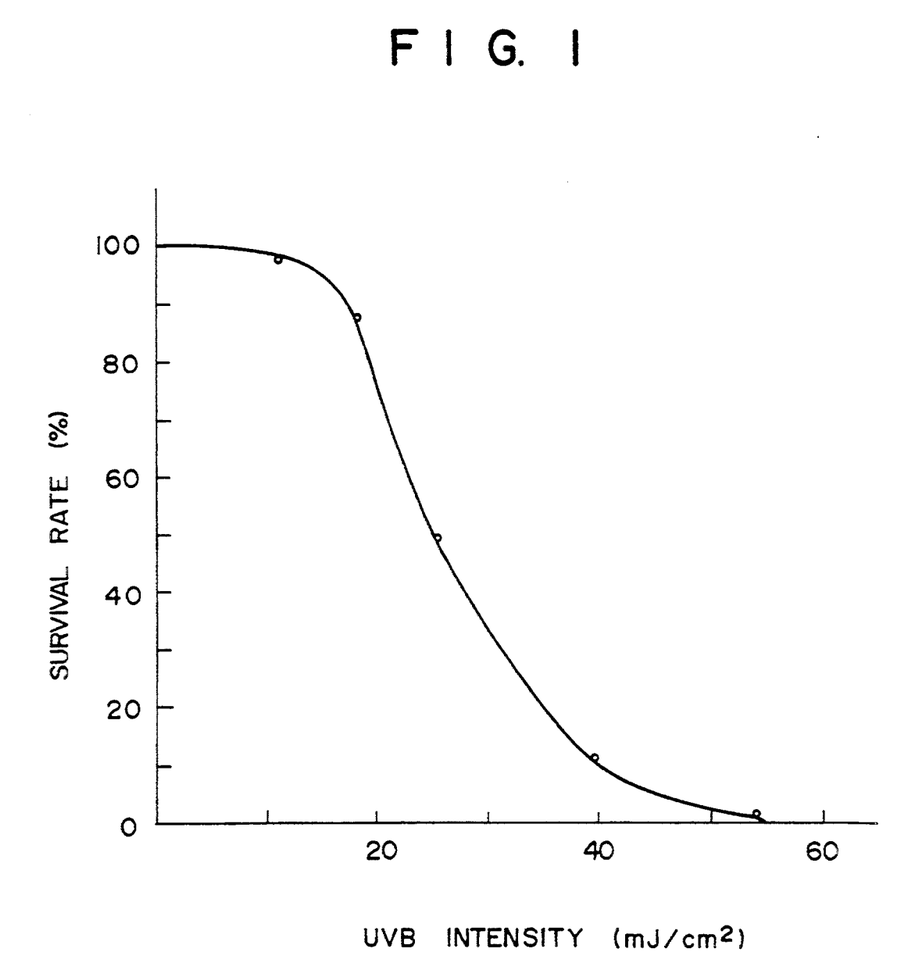
FIG. 1 shows the survival curve of L929 fibroblasts upon irradiation with UVB (wavelength: 300 nm, the same shall apply hereinafter).

After removal of the PBS (−), 2 ml of MEM medium was added to each well, followed by culturing in a 5% $CO_2$ incubator at 37° C. for 3 days. The protein content was determined, and the survival rate of the cells upon UVB irradiation was calculated according to the equation given below.

The protein content was determined by suspending the cells in the plate by treatment with 0.05% trypsin, subjecting them to ultrasonic disruption for 30 seconds in a microtube (1.5 ml, product of Eppendorf Co.) in the presence of 1 ml of PBS (−) and then to centrifugation (9,000 rpm, 20 minutes), and measuring the protein content of the supernatant using a Protein Measuring Kit (product of Bio-Rad Co.).

$$\text{Survival rate (\%)} = \frac{\text{Protein content of UVB-irradiated cells}}{\text{Protein content of non-UVB-irradiated cells}} \times 100$$

FIG. 1 shows the survival curve of L929 fibroblasts upon irradiation with UVB.

2) UVB-absorbing effect of microbial melanin

Microbial melanin (0.1 g) was completely dissolved in 100 ml of a 0.1% aqueous solution of sodium hydroxide, and then one PBS tablet (product of Takara Shuzo Co., Ltd.) was dissolved in the solution. The solution was adjusted to pH 7 with hydrochloric acid, and was sterilized using an autoclave (121° C. 15 minutes) to prepare a microbial melanin.phosphate buffer solution (microbial melanin/PBS).

L929 fibroblasts were cultured in the same manner as in 1) above, and then washed with PBS (−). The microbial melanin/PBS appropriately diluted with PBS (−) was poured into wells in an amount of 1 ml/well, followed by irradiation with UVB giving a 50% survival rate and UVB giving a 4% survival rate.

The cells were washed with PBS (−), and after removal of the PBS (−), 2 ml of MEM medium was added thereto, and culturing was carried out in the same manner as in 1) above. The protein content was determined, and the survival rate of the cells upon UVB irradiation was calculated.

Figure 2:
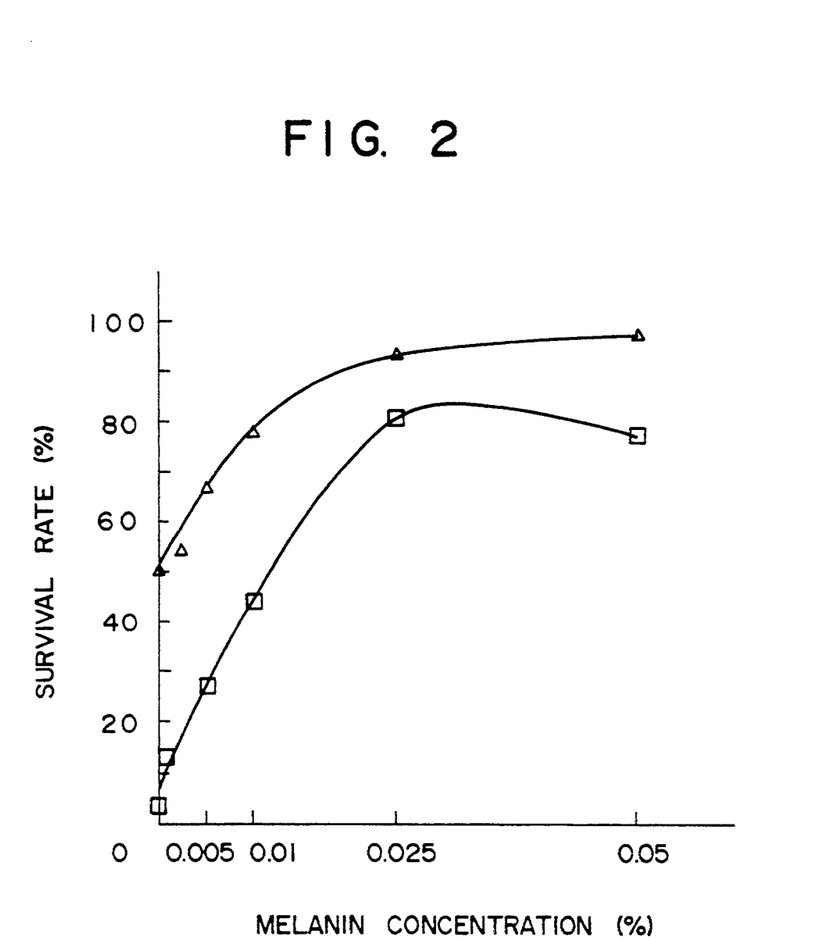
FIG. 2 shows the survival rates of L929 fibroblasts upon irradiation with UVB after the treatment with microbial melanin at different concentrations. In this figure, Δ indicates the survival rate of the cells upon UVB irradiation giving a 50% survival rate, and □ indicates the survival rate of the cells upon UVB irradiation giving a 4% survival rate.

The results are shown in FIG. 2.

From the above results, it can be seen that the survival rate of the cells upon UVB irradiation increased until the melanin concentration reached 0.025%, and thereafter, the survival rate was only slightly lowered.

3) UVB-absorbing effect of microbial melanin film

Microbial melanin (0.1 g) was completely dissolved in 100 ml of a 0.1% aqueous solution of sodium hydroxide. The solution was adjusted to pH 7 with hydrochloric acid, and then sterilized using an autoclave (121° C., 15 minutes) to prepare a 1% aqueous solution of microbial melanin.

Ten grams of the 1% aqueous solution of microbial melanin and 10 g of acrylic resin (product of Mitsubishi Petrochemical Co., Ltd.) were dissolved in ethanol to make a total amount of 100 g. Ten grams of the obtained solution was poured uniformly onto the cover of a 6-well microplate and allowed to dry overnight at 45° C. whereby a 0.1% microbial melanin film was prepared.

L929 fibroblasts were cultured in the same manner as in 1) above, and the MEM medium was removed. After the cells were washed with PBS (−), 1 ml of PBS (−) was poured into each well, and the above microbial melanin film was laid thereon, followed by irradiation with UVB with varied intensity.

The cells were washed with PBS (−), and after removal of the PBS (−), 2 ml of MEM medium was added thereto, and culturing was carried out in the same manner as in 1) above. The protein content was determined, and the survival rate of the cells upon UVB irradiation was calculated.

As a control, the same procedure as described above was repeated except that the cells were not irradiated with UVB, and the survival rate of the cells was calculated.

Figure 3:
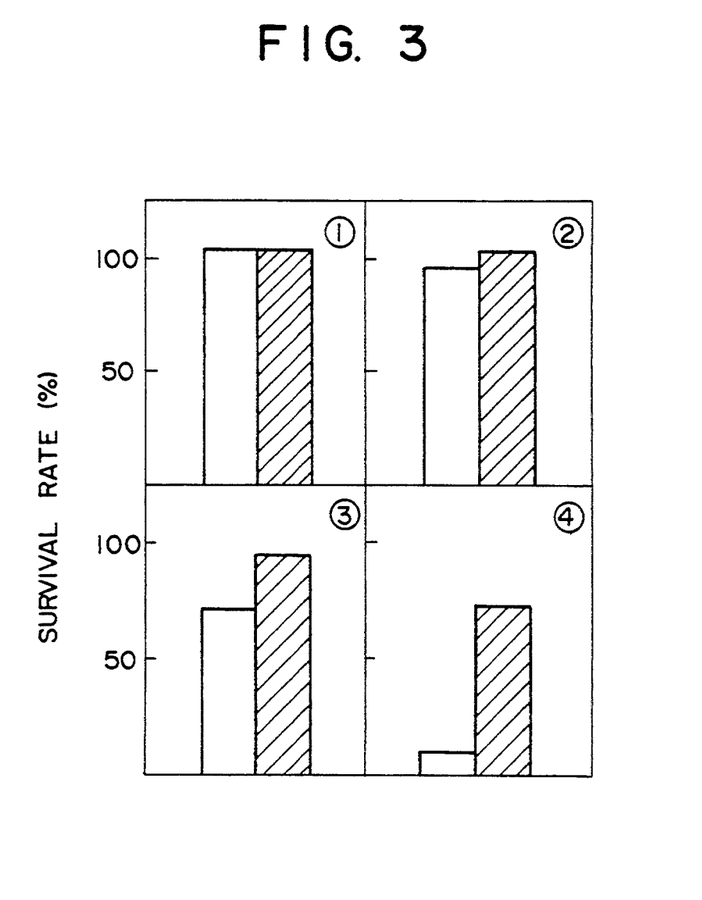
FIGS. 3①, ②, ③ and ④ show the survival rates of L929 fibroblasts coated with a microbial melanin film upon UVB irradiation (wavelength: 250 nm) at UVB strengths of 39.6 mJ/cm$^2$, 61.2 mJ/cm$^2$, 104.4 mJ/cm$^2$ and 212.4 mJ/cm$^2$ respectively in the figure, □ indicates the survival rate of the control group, and ■ indicates the above-mentioned survival rate.

The results are shown in FIG. 3.

From the above results, it is apparent that the survival rate of the cells upon UVB irradiation at 104.4 mJ/cm$^2$ and 212.4 mJ/cm$^2$ increases.

TEST EXAMPLE 2

The microbial melanin used in the present invention was examined for safety by the human 48-hour closed patch test [Nippi Kaishi, 80(5), 301–314, 1970], the single oral lethal toxicity test [No. 118 of Evaluation and Registration Division, Ministry of Health and Welfare (Feb. 15, 1984), Guidelines on Toxicity Tests Required for Application Approval for Production (or Import) of Medicines (1)] and the photosensitization test (Nishinihon Hifukagakukaishi, vol. 42, No. 5).

The results are shown in Table 1.

TABLE 1

| Test | Result |
| --- | --- |
| Human 48-hr closed patch test | Negative (44 cases) 24 males, 20 females |
| Single oral lethal toxicity test | LD$_{50}$ 2000 mg/kg or more*[1] |
| Photosensitization test | Negative*[2] |

*[1]:Test animal: CD-1 (ICR) mice
*[2]:Test animal: Hartley guinea pigs
Positive control substance: TCSA (3,3′,4′,5-tetrachlorosalicylanilide)

From the above results, it can be seen that the microbial melanin is highly safe and can be safely used in cosmetics.

TEST EXAMPLE 3

The different color tones of the microbial melanin-coated pigments of the present invention, depending on the type of carrier (pigment) and the coating concentration of the microbial melanin, were examined according to the same method as in Comparative Example 1 below, and were indicated by the values L, a and b.

The results are shown in Table 2.

TABLE 2

| Carrier pigment | Color tone | Coating concentration of microbial melanin (%) | | |
| --- | --- | --- | --- | --- |
| | | 0.5 | 1.0 | 2.0 |
| Titanium Dioxide | L | 45.1 | 42.5 | 40.3 |
| | a | 8.7 | 9.1 | 9.1 |
| | b | 10.8 | 11.3 | 11.7 |
| Sericite | L | 43.73 | 41.0 | 36.29 |
| | a | 11.54 | 11.55 | 10.97 |
| | b | 14.47 | 14.15 | 13.11 |
| Talc | L | 40.22 | 37.28 | 32.25 |
| | a | 10.30 | 9.91 | 9.89 |
| | b | 10.86 | 10.42 | 10.39 |
| Nylon powder | L | 42.86 | 27.87 | 33.15 |
| | a | 10.70 | 11.01 | 10.85 |
| | b | 14.51 | 14.54 | 14.18 |

From the above results, it can be seen that the color tone of the microbial melanin-coated pigment changes depending on the type of pigment used as the carrier.

TEST EXAMPLE 4

The ultraviolet-ray-blocking effect of cosmetics containing the melanin-coated pigment of the present invention are indicated by SPF (Sun Protection Factor) values below.

The measurement of the SPF was carried out in accordance with the "Standards for SPF Measurement" of the Japan Cosmetic Industry Association.

The sunscreen cream obtained in Example 14 above was used as the sample for SPF measurement in the present invention (listed as "sunscreen cream" in Table 3).

A cream prepared by the same procedure as in Example 14 except that the ingredients (1) and (2) in the composition were not coated with melanin was used as the control sample for SPF measurement (listed as "control" in Table 3).

The results are shown in Table 3.

TABLE 3

| SPF measurement sample | Measured SPF value |
| --- | --- |
| Sunscreen cream | 24 |
| Control | 13 |

From the above results, it can be seen that the cosmetics containing the melanin-coated pigment of the present invention exhibit a very high SPF value, and thus have an excellent ultraviolet-ray-blocking effect.

COMPARATIVE EXAMPLE 1

The color tone and tinctorial power of microbial melanin, synthetic melanin, sepia melanin, black iron oxide and carbon black (hereinafter referred to as black pigments) were compared.

Titanium dioxide was kneaded with each of the above-mentioned black pigments to make dispersions, and the color tone and tinctorial power were measured in a disperse system.

That is, a composition of 0.04% black pigment, 1.96% titanium dioxide, 2.0% polyvinyl alcohol, 5.0% acrylic resin, 73.0% 1,3-butylene glycol and 18.0% purified water was thoroughly kneaded using a 3-roll mill, and the obtained uniform paste was used as the sample of the disperse system.

The microbial melanin and the synthetic melanin were also examined in a coating system.

That is, a composition of 2.0% titanium dioxide coated with 2% microbial melanin or synthetic melanin, 2.0% polyvinyl alcohol, 5.0% acrylic resin, 73.0% 1,3-butylene glycol and 18.0% purified water was thoroughly kneaded using a 3-roll mill, and the obtained uniform paste was used as the sample of the coating system.

Certain amounts of the above-mentioned samples were applied to a hiding power test paper having a white side and a black side, and were pressed to a thickness of 0.20 mm using a Doctor blade, followed by drying to form films. Each of the samples were subjected to the measurement using a color and color-difference meter (MINOLTA model CR-200), and the color tones were indicated by L, a and b. The tinctorial power was compared on the basis of the lightness.

The results are shown in Table 4.

TABLE 4

| Black pigment in measurement sample | System | L | a | b |
|---|---|---|---|---|
| Microbial melanin | Disperse system | 78.7 | 4.3 | 4.6 |
|  | Coating system | 73.8 | 5.5 | 8.6 |
| Synthetic melanin | Disperse system | 75.7 | 4.8 | 4.2 |
|  | Coating system | 88.3 | 5.8 | 7.2 |
| Sepia melanin | Disperse system | 76.3 | 2.1 | 3.9 |
| Black iron oxide | Disperse system | 49.5 | 7.9 | 9.7 |
| Carbon black | Disperse system | 30.2 | 5.0 | 4.6 |

L: Lightness [measured with a hiding power test paper (white side)]
a,b: Chromaticity From the above results, it is seen that the microbial melanin exhibits a color tone close to that of the synthetic melanin, which is different from the jet-black color exhibited by black iron oxide and carbon black, thus presenting a warm, natural tint.

A cosmetic which contains the microbial melanin-coated pigment of the present invention provides a soft tint which is compatible with the color of skin.

In addition, it can be seen that the color tone of titanium dioxide coated with the microbial melanin is characterized by high coloring and high saturation compared with dispersed products, and that when the microbial melanin is contained in a cosmetic, coating systems provide products of a higher stability as compared with disperse systems.

COMPARATIVE EXAMPLE 2

Purified water was added to 0.1 g of microbial melanin, synthetic melanin or sepia melanin and 0.1 g of sodium hydroxide to prepare 100 ml of solution, and the pH was adjusted to 7 with hydrochloric acid.

To 0.1 g of dl-α-tocopherol was added ethanol to prepare 100 ml of solution.

To 0.1 g of ascorbic acid was added purified water to prepare 100 ml of solution.

To 5.02 mg of an 80% cumene hydroperoxide (hereinafter abbreviated to CPO) solution was added purified water to prepare 100 ml of solution (264 nmol/ml).

The microbial melanin solution, the ascorbic acid solution, the dl-α-tocopherol solution, the synthetic melanin solution or the sepia melanin solution was added to a system in which CPO was reacted with a methylene blue derivative in the presence of hemoglobin as a catalyst, using Determiner LPO (product of Kyowa Medex Co., Ltd.) as a reaction reagent, thereby producing an equimolar amount of methylene blue which developed the color of the system. The anti-oxidizing property of the microbial melanin, ascorbic acid, dl-α-tocopherol, the synthetic melanin and the sepia melanin was determined on the basis of the degree of inhibition of the production of methylene blue.

That is, the test sample, the standard sample and the blank test sample shown in Table 5 were prepared, and in accordance with the directions for the use of the above-mentioned reagent which were annexed thereto, the absorbance of each of the reacted samples at a wavelength of 675 nm was measured with the blank test sample as a control, and the lipid peroxide elimination rate was calculated by the equation given below.

TABLE 5

|  | Test sample (S) | Standard sample (Std) | Blank test sample (B) |
|---|---|---|---|
| Solution of microbial melanin, ascorbic acid, dl-α-tocopherol, synthetic melanin or sepia melanin | 0.5 ml | — | — |
| CPO solution | 0.1 ml | 0.1 ml | — |
| Purified water | — | 0.5 ml | 0.6 ml |

$$\text{Lipid peroxide elimination rate (\%)} = \left(1 - \frac{A_S - A_B}{A_{std} - A_B}\right) \times 100$$

In the equation, $A_S$ indicates the absorbance of the test sample, $A_{std}$ the absorbance of the standard sample, and $A_B$ the absorbance of the blank test sample.

The lipid peroxide elimination rates of the microbial melanin, ascorbic acid, dl-α-tocopherol, the synthetic melanin and the sepia melanin at a concentration of 0.014% are shown in Table 6.

TABLE 6

|  | Lipid peroxide elimination rate (%) |
|---|---|
| Ascorbic acid | 97.4 |
| dl-α-tocopherol | 72.4 |
| Synthetic melanin | 90.2 |
| Sepia melanin | 57.7 |
| Microbial melanin | 48.5 |

The anti-oxidizing property of the microbial melanin, ascorbic acid, dl-α-tocopherol, the synthetic melanin and the sepia melanin can be expressed as the lipid peroxide elimination rate.

From the above results, it can be seen that the microbial melanin used in the present invention has an anti-oxidizing property.

INDUSTRIAL APPLICABILITY

The present invention provides a melanin-coated pigment which is highly safe and has high coloring and high saturation tone, and a cosmetic containing the pigment.

The melanin-coated pigment can be used as a flesh-colored or gray-colored coloring pigment in paint, ink, cosmetics, and the like. When used in cosmetics, it is expected to be also effective for the absorption of ultraviolet rays and for anti-oxidation.

I claim:

1. A melanin-coated pigment which is prepared by coating a carrier with a readily alkali-soluble natural melanin.

2. A melanin-coated pigment according to claim 1, wherein the carrier is an inorganic or organic pigment.

3. A melanin-coated pigment according to claim 2, wherein the carrier is selected from the group consisting of titanium dioxide, talc, sericite, mica, micaceous titanium, montmorillonite, kaolin, alumina, magnesium oxide, cesium oxide, silica, muscovite, barium sulfate, aluminum silicate, aluminum magnesium silicate, sodium magnesium silicate, calcium silicate, iron oxide, calcium carbonate, pumice powder and ultramarine.

4. A melanin-coated pigment according to claim 1, wherein the carrier is selected from the group consisting of silicon resin, cellulose and silk powder.

5. A melanin-coated pigment according to claim 1, wherein the natural melanin is a melanin produced by a microorganism belonging to the genus Aureobasidium, Aspergillus or Streptomyces.

6. A cosmetic containing a melanin-coated pigment according to claim 1, 2, 3, 4 or 5.

* * * * *

UNITED STATES PATENT AND TRADEMARK OFFICE
CERTIFICATE OF CORRECTION

PATENT NO. : 5,380,359
DATED : January 10, 1995
INVENTOR(S) : SHINKICHI HONDA, ET AL.

It is certified that error appears in the above-identified patent and that said Letters Patent is hereby corrected as shown below:

COLUMN 4

Line 48, "respectively in" should read --respectively. In--.

COLUMN 6

Line 22, "(2) Melanin-coated mica    55%" should read
--(1) Melanin-coated titanium dioxide    9.0%
   (2) Melanin-coated mica              55.0%--.

COLUMN 11

Line 9, "dispersed-with" should read --dispersed with--.

COLUMN 12

Line 31, "(121°C." should read --(121°C.,--.

UNITED STATES PATENT AND TRADEMARK OFFICE
CERTIFICATE OF CORRECTION

PATENT NO. : 5,380,359
DATED : January 10, 1995
INVENTOR(S) : SHINKICHI HONDA, ET AL.

It is certified that error appears in the above-identified patent and that said Letters Patent is hereby corrected as shown below:

<u>COLUMN 16</u>

Line 46, "I claim:" should read --What is claimed is:--.
  Line 61, "of" should read --of nylon,--.

Signed and Sealed this

Twenty-seventh Day of June, 1995

Attest:

BRUCE LEHMAN

*Attesting Officer*        *Commissioner of Patents and Trademarks*